(12) United States Patent
Rubenchik et al.

(10) Patent No.: US 10,234,411 B2
(45) Date of Patent: Mar. 19, 2019

(54) SYSTEM AND METHOD FOR THE DIRECT CALORIMETRIC MEASUREMENT OF LASER ABSORPTIVITY OF MATERIALS

(71) Applicants: Alexander Rubenchik, Livermore, CA (US); Ilya V. Golosker, Livermore, CA (US); Mary M. LeBlanc, Livermore, CA (US); Scott C. Mitchell, Tracy, CA (US); Sheldon S. Wu, Pleasanton, CA (US)

(72) Inventors: Alexander Rubenchik, Livermore, CA (US); Ilya V. Golosker, Livermore, CA (US); Mary M. LeBlanc, Livermore, CA (US); Scott C. Mitchell, Tracy, CA (US); Sheldon S. Wu, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 99 days.

(21) Appl. No.: 15/213,210

(22) Filed: Jul. 18, 2016

(65) Prior Publication Data
US 2017/0016839 A1    Jan. 19, 2017

Related U.S. Application Data

(60) Provisional application No. 62/194,132, filed on Jul. 17, 2015.

(51) Int. Cl.
*G01N 25/20* (2006.01)
*G01K 17/04* (2006.01)
(Continued)

(52) U.S. Cl.
CPC ............ *G01N 25/20* (2013.01); *G01N 25/48* (2013.01); *G01K 17/00* (2013.01); *G01K 17/04* (2013.01);
(Continued)

(58) Field of Classification Search
CPC .... G01N 25/20; G01N 25/48; G01N 25/4846; G01N 25/4853; G01N 25/486; G01K 17/00; G01K 17/04
See application file for complete search history.

(56) References Cited

U.S. PATENT DOCUMENTS 3,165,915 A * 1/1965 Parker .................... G01N 25/00
374/43
3,348,047 A * 10/1967 Clifford .................... G01J 5/12
250/338.1

(Continued)

OTHER PUBLICATIONS

Rubenchik et al. "Temperature dependent 780-nm laser absorption by engineering grade aluminum, titanium, and steel alloy surfaces" Lawrence Livermore National Laboratory LLNL-JRNL0635613. Apr. 22, 2013 <https://e-reports-ext.llnl.gov/pdf/753973.pdf>.*

(Continued)

*Primary Examiner* — Jonathan M Dunlap
(74) *Attorney, Agent, or Firm* — James S. Tak

(57) ABSTRACT

A method and system for calorimetrically measuring the temperature-dependent absorptivity of a homogeneous material dimensioned to be thin and flat with a predetermined uniform thickness and a predetermined porosity. The system includes a material holder adapted to support and thermally isolate the material to be measured, an irradiation source adapted to uniformly irradiate the material with a beam of electromagnetic radiation, and an irradiation source controller adapted to control the irradiation source to uniformly heat the material during a heating period, followed by a cooling period when the material is not irradiated. A thermal sensor measures temperature of the material during the heating and cooling periods, and a computing system first calculates temperature-dependent convective and radiative thermal losses of the material based on the measured temperature of the material during the cooling period when (Continued)

beam intensity is zero, followed by calculation of the temperature-dependent absorptivity of the material based on the temperature-dependent convective and radiative thermal losses determined from the cooling period.

11 Claims, 2 Drawing Sheets

(51) Int. Cl.
  *G01N 25/48* (2006.01)
  *G01K 17/00* (2006.01)
(52) U.S. Cl.
  CPC ....... *G01N 25/486* (2013.01); *G01N 25/4846* (2013.01); *G01N 25/4853* (2013.01)

(56) References Cited

U.S. PATENT DOCUMENTS

| | | | | |
|---|---|---|---|---|
| 4,722,609 A | * | 2/1988 | Epstein | G01K 17/20 250/252.1 |
| 4,812,050 A | * | 3/1989 | Epstein | G01K 17/20 250/252.1 |
| 2002/0146345 A1 | * | 10/2002 | Neilson | G01N 25/482 422/51 |
| 2010/0258726 A1 | * | 10/2010 | Zhang | G01J 5/02 250/336.1 |
| 2013/0039381 A1 | * | 2/2013 | Pavageau | G01N 15/02 374/29 |
| 2013/0058376 A1 | * | 3/2013 | Pavageau | G01N 15/02 374/29 |
| 2015/0185091 A1 | * | 7/2015 | Hasegawa | B23K 26/032 374/32 |

OTHER PUBLICATIONS

Rubenchik et al. "Direct measurements of the temperature-dependent laser absorptivity of metal powder". LAwrence Livermore National Laboratory LLNL-JRNL-669601. Apr. 13, 2015 <https://e-reports-ext.llnl.gov/pdf/791275.pdf>.*
Wu et al. "Direct Absorptivity Measurements of Metallic Powders Under 1-Micron Wavelength Laser Light". Lawrence Livermore National Laboratory LLNL-CONF-658053. Jul. 31, 2014 <https://e-reports-ext.llnl.gov/pdf/779044.pdf>.*

* cited by examiner

SYSTEM AND METHOD FOR THE DIRECT CALORIMETRIC MEASUREMENT OF LASER ABSORPTIVITY OF MATERIALS

CROSS-REFERENCE TO RELATED APPLICATIONS

This application claims the benefit of U.S. provisional application No. 62/194,132 filed Jul. 17, 2015.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Additive manufacturing is a rapidly growing field with a wide range of applications. Presently, there exists a need for the measurement of powder absorptivity for use in the analysis and modeling of laser-material interactions in the additive manufacturing build process. The absorptivity of powder depends not only on material type and laser wavelength; it is sensitive to the size distribution of the particles, particle shape, powder thickness and porosity.

Existing systems, such as for example the system described in *Absorptance of powder materials suitable for laser sintering* by N. Tolochko et al, (Rapid Prototyping Journal 6.155. 2000), measure the reflected light from the powder with the help of an integrating sphere and are typically complex. The distribution of the scattered light is unknown and even the small absorption in the integrating sphere coating can affect the result.

There is therefore a need for a simple compact system and method for performing fast, accurate measurements of laser absorptivity of powders.

SUMMARY

One aspect of the present invention includes a calorimetric method of measuring the temperature-dependent absorptivity of a material, comprising: providing a homogeneous material dimensioned to be thin and flat with a predetermined uniform thickness and a predetermined porosity; thermally isolating the material; uniformly irradiating the material with a beam of electromagnetic radiation having a predetermined intensity to uniformly heat the material during a heating period, followed by a cooling period when the material is not irradiated and the intensity of the beam is zero; measuring the temperature of the material during the heating and cooling periods; determining temperature dependent convective and radiative thermal losses of the material based on the measured temperature of the material during the cooling period when beam intensity is zero, and the thickness and porosity of the material; and determining the temperature-dependent absorptivity of the material based on the temperature-dependent convective and radiative thermal losses determined from the cooling period, the thickness and porosity of the material, and the intensity of the beam.

Other aspects of the calorimetric method of measuring the temperature dependent absorptivity of a material of the present invention include one or more of the following: (1) wherein the material is a powder or liquid provided in a thermally conductive container having a container volume with a uniform and shallow depth, and with the powder or liquid conformably filling the container volume to capacity to have the predetermined thickness and the predetermined porosity; and wherein the temperature of the powder or liquid is measured by measuring the temperature of the container; (2) wherein the container has an opening defined by a rim into the container volume; and wherein the powder is made to conformably fill the container volume to capacity by using an implement adapted to remove excess powder in the container volume when run along the rim of the opening; (3) wherein the powder or liquid material is thermally isolated by suspending the powder or liquid-filled container on at least two wires suspended between end supports; and (4) wherein a solid material is thermally isolated by suspending the solid material on at least two wires suspended between end supports.

Another aspect of the present invention include a system for calorimetrically measuring the temperature-dependent absorptivity of a homogeneous material dimensioned to be thin and flat with a predetermined uniform thickness and a predetermined porosity, comprising: a material holder adapted to support and thermally isolate the material to be measured; an irradiation source adapted to uniformly irradiate the material with a beam of electromagnetic radiation; an irradiation source controller adapted to control the irradiation source to uniformly heat the material with a beam having a predetermined intensity during a heating period, followed by a cooling period when the material is not irradiated and the intensity of the beam is zero; a thermal sensor adapted to measure temperature of the material during the heating and cooling periods; and a computing system operably connected to the thermal sensor, and adapted to determine temperature-dependent convective and radiative thermal losses of the material based on the measured temperature of the material during the cooling period when beam intensity is zero, and the thickness and porosity of the material, and to determine the temperature-dependent absorptivity of the material based on the temperature-dependent convective and radiative thermal losses determined from the cooling period, the thickness and porosity of the material, and the intensity of the beam.

Other aspects of the system of the present invention include one or more of the following: (1) wherein the material holder comprises a thermally conductive container having a container volume with a uniform and shallow depth so that a powder or liquid material conformably filling the container volume to capacity has the predetermined thickness and the predetermined porosity; and wherein the thermal sensor is adapted to measure temperature of the powder or liquid material by measuring the temperature of the container; (2) wherein the container has an opening defined by a rim into the container volume, and the system further comprises an implement adapted to remove excess powder in the container volume when run along the rim of the opening; (3) wherein the material holder further comprises at least two wires suspended between end supports for suspending the powder or liquid-filled container thereon to thermally isolate the powder or liquid material; (4) wherein the material holder further comprises at least two wires suspended between end supports for suspending a solid material thereon to thermally isolate the solid material; and (5) wherein the computing system operably is operably connected to the irradiation controller for receiving start and stop times of the irradiation source for identifying the heating and cooling periods.

The present invention is generally directed to a system and method for the direct calorimetric measurement of powder absorptivity, and which eliminates the effect of convective and radiative loss. Generally, a thin and flat homogeneous material is provided and thermally isolated. The material may be a powder, liquid, or solid (i.e. bulk solid). In the case of measuring powders or liquids for absorptivity, a flat container or tray (e.g. disc-shaped container) having a shallow container volume is provided and filled with powder or liquid to produce a thin layer of powder or liquid in the container volume. Dimensioned in this manner, the materials dimensions as well as the porosity are be predetermined and known based on the filled-to-capacity container volume and a measured weight of the material filling the container volume. The material is also thermally isolated by various methods. The material is then uniformly irradiated by laser or diode array light to uniformly heat the material during a heating period, followed by a cooling period in which irradiation is removed and beam intensity is zero. The temperature of the material is measured using thermal sensors operably connected (contactedly or remotely) to the container. And a computing system, which may include for example a processor, data storage, display, etc. first calculates and determines temperature-dependent convective and radiative thermal losses of the material based on the measured temperature of the material during the cooling period when beam intensity is zero, and the thickness and porosity of the material. Based on the temperature-dependent convective and radiative thermal losses determined from the cooling period, the computing system then calculates and determines the temperature-dependent absorptivity of the material. The system provides the temperature dependent absorptivity measurements up to the powder melting point.

These and other implementations and various features and operations are described in greater detail in the drawings, the description and the claims.

DETAILED DESCRIPTION

Figure 1:
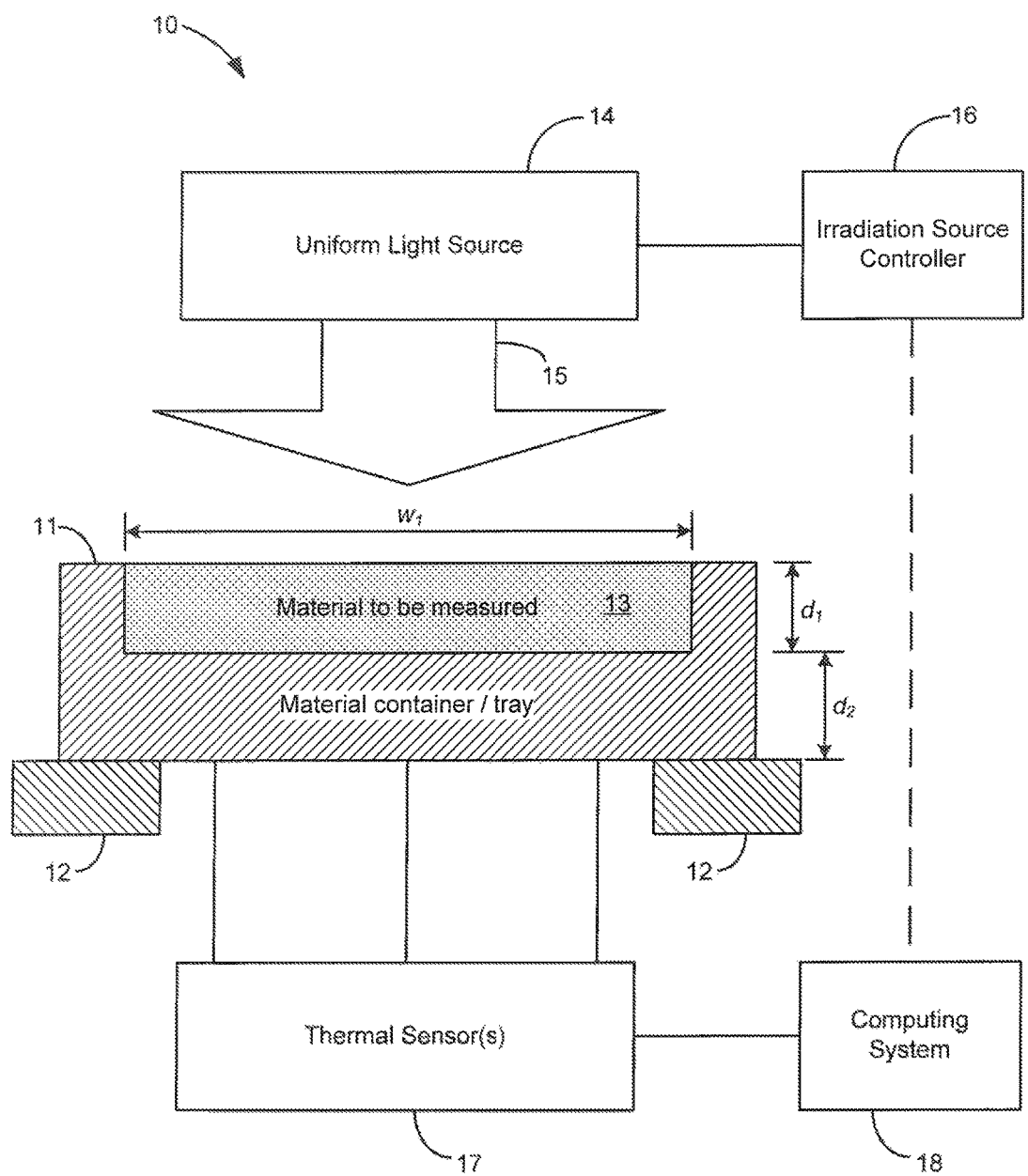
FIG. 1 is a schematic view of an example embodiment of the system of the present invention.

Turning now to the drawings, FIG. 1 shows an example embodiment of the system for the direct calorimetric measurement of the laser absorptivity of a material of the present invention, generally indicated at 10. The system is shown having a material container or tray 11 having an open cavity for receiving a material to be measured (shown at 13 filling the cavity). The open cavity is shown having a width $w_1$ and a depth $d_1$, and the material container/tray is shown having a thickness $d_2$ between the material to be measured and an outer surface where thermal sensors 17 are shown positioned at various locations to determine temperature and temperature uniformity of the material container/tray. The container is also shown supported by a thermal isolation structure, generally shown at 12. The container 11 and the thermal isolation structure 12 may be characterized together as a material holder adapted to support and thermally isolate the material to be measured. It is appreciated that the thermal sensor(s) 17 are shown schematically connected to the material container/tray, and that the connection may be direct and physical, such as for example if thermocouples are directly attached, or may be an indirect remote, such as for example if a remote sensor is utilized. The system is also shown including an irradiation source controller 16 which is adapted to control a uniform irradiation source 14 to uniformly heat the material with a beam 15 having a predetermined intensity during a heating period, followed by a cooling period when the material is not irradiated and the intensity of the beam is zero. A computing system 18 is also provided operably connected to the thermal sensors and adapted to use the thermal readings to determine the absorptivity of the material, as further described below. In one example embodiment, the computing system may also be operably connected to the irradiation controller (shown by broken line in FIG. 1) for receiving start and stop times of the irradiation source for identifying the heating and cooling periods.

Figure 2:
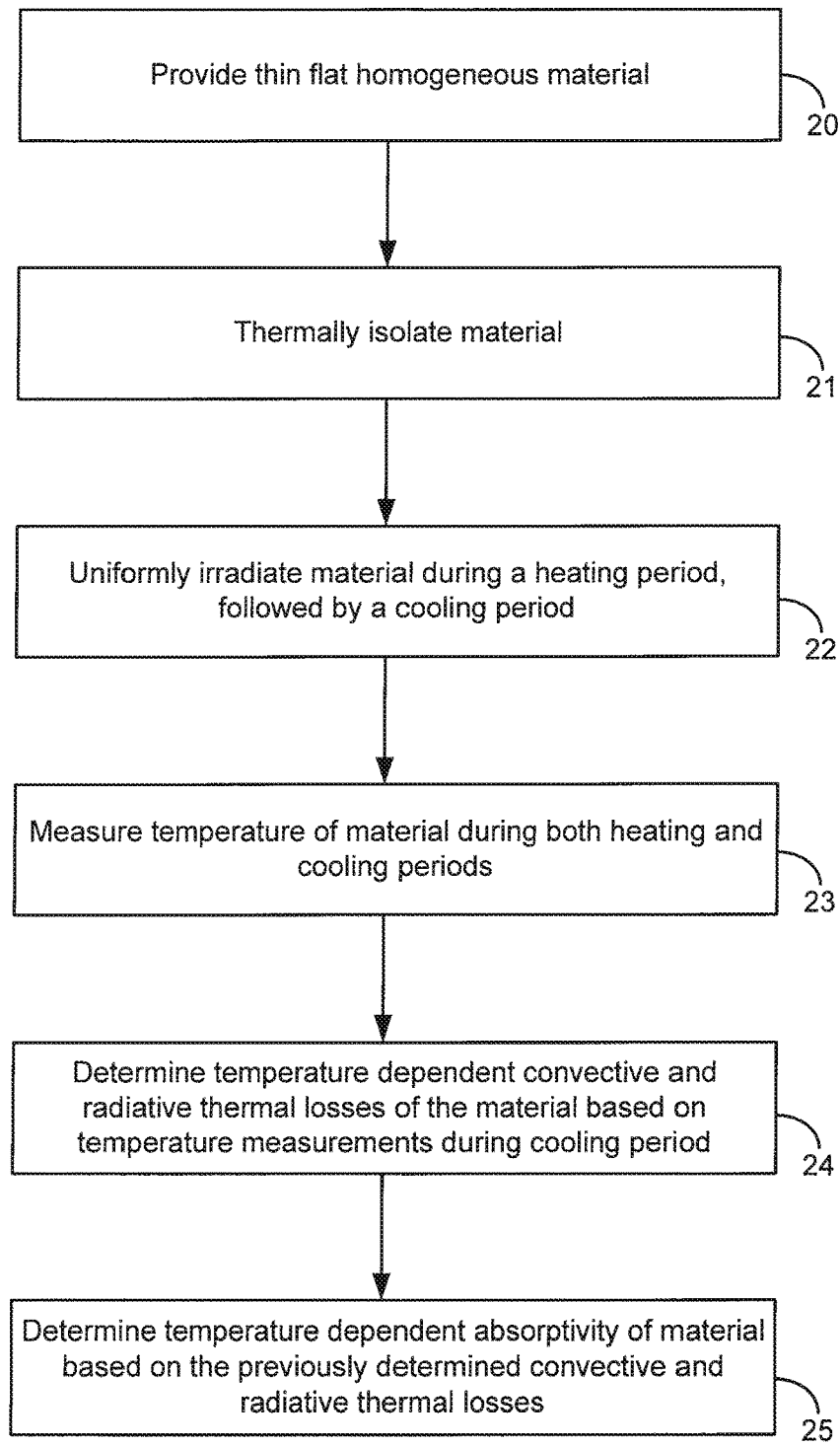
FIG. 2 is a flow chart of an example embodiment of the method of the present invention.

FIG. 2 shows an example embodiment of a method for the direct calorimetric measurement of the laser absorptivity of a material of the present invention. First, a thin flat homogenous material is provided at 20, which may be a powder, liquid, or a bulk solid. In the case of powders in particular, a thin layer of powder may be placed on a thin disc made from refractory metal or other high thermally conductive material. And various powder laying techniques may be used, including for example, a hard blade, a soft blade and roller. Each technique will result in a different powder distribution with significant differences in porosity. In the case of bulk solids, the having predetermined dimensions. Next at 21, the material sample provided in the material container is then thermally isolated, such as by a thermal insulator structure (e.g. a wire suspension). The thermal insulator structure may also be constructed from a refractory metal or other type of material that does not absorb a significant amount of the incident radiation nor affect the temperature distribution in the target.

At 22, the thermally isolated material is then uniformly irradiated by a uniform laser or diode array beam during both heating and cooling periods.

Next at 23, measurements of the temperature evolution are made during heating and cooling in order to eliminate the effect of the convective and radiative losses, and thereby directly measure material absorptivity. For powder materials in particular, the special design of the flat container provides direct powder porosity measurements and the possibility of performing the measurements up to the powder melting point. The temperature changes are measured by the thermal sensors (e.g. thermocouples connected to the rear side/outer surface of the disc, or a remote thermal sensor directed at the rear side/outer surface of the disc). And the heating process may be, for example on the scale of seconds, which is sufficient slow so that the temperature will be uniform across the material and will be uniform across the disc due to irradiation uniformity.

Next at 24, a computing system determines temperature dependent convective and radiative thermal losses of the material based on temperature measures during the cooling period. Consider a thin layer of powder with thickness $d_1$ on a flat disc of refractory metal with thickness $d_2$ uniformly illuminated by light with intensity I. For absorptivity of powder (or melt), assuming uniform temperature through the foil, the temperature evolution is:

$$(\rho_1 c_1 d_1 + \rho_2 c_2 d_2)\frac{dT}{dt} = A(T)I - Q(T) \qquad (1)$$

where A(T) is the absorptivity, Q(T) the thermal losses including convective and radiative, I the density, c the specific heat, d the thickness, and subscript "1" for powder and "2" the substrate. NOTE: An important parameter in this process is the powder density (porosity). The disc is filled with powder and the extra material is removed by a hard blade, soft blade or roller pin rolled along the rim, mimicking the powder deposition in a real system. Weighing the disc with powder and without allows one to determine the powder weight and porosity.

Consider a flat top, finite duration heating pulse. First the temperature during cooling when I=0 is measured and will determine the convective and radiative losses Q(T).

Finally, at 25, the computing system determines the temperature dependent absorptivity of the material based on the previously determined convective and radiative thermal losses according to Equation (1). In particular, Equation (1) is used to determine the temperature dependent absorptivity considering the temperature evolution during the heating stage. Also, the powder density (porosity) required in Equation (1) is determined from the dimensions and parameters of the material contained in the container/tray of the present invention. The target disc is dimensioned so that the open cavity for receiving the material has a predetermined width ($w_1$ in FIG. 1) and a rim with a predetermined height ($d_1$) to determine the powder thickness. The height is determined by the shallow depth of the container volume of the disc-shaped container/tray. The disc is filled with powder and the extra material is removed by a blade or roller moved along the rim, mimicking the powder deposition in the real system. Weighing the disc with powder (using a weight scale not shown in the Figures) and without the powder weight of the volume $\pi h d^2/4$ can be determined, as well as calculate the porosity of the material.

Various types of materials may be measured for absorptivity, including powders, liquids, and solids. However, the material is dimensioned to be thin and flat with a predetermined uniform thickness, e.g. 1% variation of thickness, and predetermined porosity. One example thickness range of the material may be in the range of: 0.50 µm-2 mm. Some example thicknesses for various materials include: Ti Foil, 0.2 mm, 0.5 mm for Ti foil, 0.1 mm for SS Powder, and 1.6 mm for OFHC Cu foil. The material also preferably has a uniform material composition (homogeneity). For example, the irradiated area of the sample must be large compared to the areas of impurities or different material phases.

Regarding the material holder, various types of designs may be utilized which provide support and thermal isolation to the material being measured. In some embodiments, the material holder may include a thermally conductive container or tray having a container volume for containing a powder or liquid type material. Various material types which are good thermal conductors may be used for the container to enable the container to exhibit the same temperature of the material it is containing. In some embodiments, refractory metals or carbon(graphite) may be used to withstand the high applied temperatures.

Furthermore, the material holder must also operate to thermally isolate the material being measured. For example if a solid bulk material is measured, a thermally conductive container is not required, and in this case the material holder may include a thermally insulating support structure, such as for example a fused silica structure. Even in the case where a thermally conductive container is used to contain a powder or liquid material, such a thermally insulating support structure may also be utilized to thermally isolate the powder or liquid-filled container. Some example configurations for thermally isolating the material include providing a wire suspension, i.e. at least two wires suspended between end supports, upon which a solid material or a material-filled container is suspended. The wire suspension may be constructed with, for example, tungsten wire. In another example embodiment, a refractory metal holder may be used having 3 equally spaced thin arms free to move on knife-edge supports away from irradiation area.

Regarding the thermal sensor various types of thermal sensors may be used, including contact type thermal sensors such as for example, thermocouples, as well as non-contact/remote thermal sensors, such as for example infrared cameras and fiber-optic pyrometers.

Regarding the irradiation source, it is adapted to uniformly irradiate the sample. Uniformity must be sufficiently high so that the temperature of the material remains uniform across and throughout the material. Some example sources include lasers (diode, fiber, solid-state, dye, gas), LEDs, Auxiliary heating sources (electrical, lamp, RF), etc. Example intensities include the range or about 1-1000 W/cm² CW intensity on the material sample depending on temperature range desired. And the irradiation sources may operate at various wavelengths. For example, most of the modern laser processing is done with 1 µm light (welding, cutting and additive manufacturing applications). Second harmonics and wavelength ~0.8 µm and 1.5 µm may also be considered.

The computing system of the present invention may be implemented a central processor unit and memory, and may include input devices, (e.g. keyboard and pointing devices), output device (e.g. display devices), and storage devices (e.g. disk drives). The computing system may also be implemented with software programmed to perform the method described herein for calculating the absorptivity of the material.

Although the description above contains many details and specifics, these should not be construed as limiting the scope of the invention but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

We claim:

1. A calorimetric method of measuring the temperature-dependent absorptivity of a material, comprising:
   providing a homogeneous material dimensioned to be thin and flat with a predetermined uniform thickness and a predetermined porosity;
   thermally isolating the material;
   uniformly irradiating the material with a beam of electromagnetic radiation having a predetermined intensity to uniformly heat the material during a heating period, followed by a cooling period when the material is not irradiated and the intensity of the beam is zero;
   measuring the temperature of the material during the heating and cooling periods;
   determining temperature-dependent convective and radiative thermal losses of the material based on the measured temperature of the material during the cooling period when beam intensity is zero, and the thickness and porosity of the material; and
   determining the temperature-dependent absorptivity of the material based on the temperature-dependent convective and radiative thermal losses determined from the cooling period, the thickness and porosity of the material, and the intensity of the beam.

2. The method of claim 1,
   wherein the material is a powder or liquid provided in a thermally conductive container having a container volume with a uniform and shallow depth, and with the powder or liquid conformably filling the container volume to capacity to have the predetermined thickness and the predetermined porosity; and
   wherein the temperature of the powder or liquid is measured by measuring the temperature of the container.

3. The method of claim 2,
   wherein the container has an opening defined by a rim into the container volume; and
   wherein the powder is made to conformably fill the container volume to capacity by using an implement adapted to remove excess powder in the container volume when run along the rim of the opening.

4. The method of claim 2,
   wherein the powder or liquid material is thermally isolated by suspending the powder or liquid-filled container on at least two wires suspended between end supports.

5. The method of claim 1,
   wherein a solid material is thermally isolated by suspending the solid material on at least two wires suspended between end supports.

6. A system for calorimetrically measuring the temperature-dependent absorptivity of a homogeneous material dimensioned to be thin and flat with a predetermined uniform thickness and a predetermined porosity, comprising:
   a material holder adapted to support and thermally isolate the material to be measured;
   an irradiation source adapted to uniformly irradiate the material with a beam of electromagnetic radiation;
   an irradiation source controller adapted to control the irradiation source to uniformly heat the material with a beam having a predetermined intensity during a heating period, followed by a cooling period when the material is not irradiated and the intensity of the beam is zero;
   a thermal sensor adapted to measure temperature of the material during the heating and cooling periods; and
   a computing system operably connected to the thermal sensor, and adapted to determine temperature-dependent convective and radiative thermal losses of the material based on the measured temperature of the material during the cooling period when beam intensity is zero, and the thickness and porosity of the material, and to determine the temperature-dependent absorptivity of the material based on the temperature-dependent convective and radiative thermal losses determined from the cooling period, the thickness and porosity of the material, and the intensity of the beam.

7. The system of claim 6,
   wherein the material holder comprises a thermally conductive container having a container volume with a uniform and shallow depth so that a powder or liquid material conformably filling the container volume to capacity has the predetermined thickness and the predetermined porosity; and
   wherein the thermal sensor is adapted to measure temperature of the powder or liquid material by measuring the temperature of the container.

8. The system of claim 7,
   wherein the container has an opening defined by a rim into the container volume, and the system further comprises an implement adapted to remove excess powder in the container volume when run along the rim of the opening.

9. The system of claim 7,
   wherein the material holder further comprises at least two wires suspended between end supports for suspending the powder or liquid-filled container thereon to thermally isolate the powder or liquid material.

10. The system claim 6,
    wherein the material holder further comprises at least two wires suspended between end supports for suspending a solid material thereon to thermally isolate the solid material.

11. The system of claim 6,
    wherein the computing system operably is operably connected to the irradiation controller for receiving start and stop times of the irradiation source for identifying the heating and cooling periods.

* * * * *